(12) United States Patent
Vazquez et al.

(10) Patent No.: US 6,287,339 B1
(45) Date of Patent: Sep. 11, 2001

(54) SUTURELESS HEART VALVE PROSTHESIS (75) Inventors: Demetrio J. Vazquez, Rancho Santa Fe, CA (US); Louis A. Campbell; Jeffrey M. Mabrey, both of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/321,079

(22) Filed: May 27, 1999

(51) Int. Cl.$^7$ .......................................................... A61F 2/24
(52) U.S. Cl. .......................... 623/2.4; 623/2.11; 623/2.33
(58) Field of Search .................................... 623/2.1, 2.11, 623/2.14, 2.18, 2.23, 2.36, 2.38, 2.4, 2.41, 2.42

(56) References Cited

U.S. PATENT DOCUMENTS

| | | | |
|---|---|---|---|
| 3,996,623 | * 12/1976 | Kaster | 3/1.5 |
| 4,576,605 | * 3/1986 | Kaidash et al. | 623/2 |
| 5,571,175 | * 11/1996 | Vanney et al. | 623/2 |
| 5,824,069 | * 10/1998 | Lemole | 623/2 |
| 5,843,179 | * 12/1998 | Vanney et al. | 623/2 |
| 6,042,607 | * 3/2000 | Williamson, IV et al. | 623/2 |

* cited by examiner

Primary Examiner—David H. Willse
Assistant Examiner—Alvin Stewart
(74) Attorney, Agent, or Firm—Timothy L. Scott; Kenneth S. Barrow (57) ABSTRACT A heart valve prosthesis which incorporates a substantially permanently implantable abutment structure which is surgically attached to a native heart valve annulus through utilization of a resilient metal substructure having an attachment portion which moves into engagement with a native heart annulus upon being released from a retracted orientation. The system employs a positioning instrument which locates the abutment structure and associated heart valve prosthesis at the proper location for releasing the attachment components. Mechanical heart valve components including an occluder function are removably attached to the abutment structure using sutures, such that the valve function itself may be subsequently replaced.

22 Claims, 7 Drawing Sheets

SUTURELESS HEART VALVE PROSTHESIS

BACKGROUND OF THE INVENTION

Arteries and veins provide the pathways through which blood is circulated to all parts of the human body. The heart, a well-developed muscle, pumps blood through these established pathways, the blood providing needed oxygen and removing unwanted carbon dioxide. Blood containing carbon dioxide is carried to the heart by the veins where it is pumped from the right atrium through the tricuspid valve to the right ventricle. Blood is then pumped through the pulmonary valve to the lungs by the arteries where carbon dioxide is exchanged for oxygen. Oxygenated blood returns to the left atrium and is pumped through the mitral valve to the left ventricle. From the left ventricle the blood is pumped through the aortic valve and then throughout the body. Supplying oxygen and removing carbon dioxide, the blood returns by the veins to the right atrium. This process is continually repeated as the heart meets the body's need for a continuous supply of oxygen and concomitant need for removal of waste products.

In response to the transvalvular pressure gradient between systole and diastole, the cardiac valves open or close to either permit blood flow or prevent backflow. Congenital abnormalities or valve disease, which may be caused for example by calcific degeneration, rheumatic degeneration or endocarditis, may interfere with valvular performance. Incompetence, or failure of the valve to completely close, results in regurgitation with a correspondingly increased effort by the heart to pump sufficient amounts of blood to the body and lungs. Stenosis, which is a narrowing of the valve orifice, also stresses the heart as it attempts to pump an adequate volume of blood through a smaller opening. In cases involving mitral or aortic stenosis, surgical treatment may involve reconstruction of the valve by mitral commissurotonomy or valvuloplasty. Complications after surgery include inadequate relief of stenosis due to severe subvalvular stenosis or mitral regurgitation due to excessive commissurotonomy. These procedures, with potential associated complications, may be appropriate in a limited number of cases, however, reconstruction of an aortic valve or stenotic mitral heart valve normally is not feasible, and the surgeon must replace the defective valve with a prosthetic one. Reconstruction of an incompetent mitral valve is a common procedure, but in some cases the mitral valve pathology is so severe replacement is required. Of the four heart valves, the most commonly replaced are the mitral valve and the aortic valve. For information on aortic valve surgery and mitral valve surgery, see:

1.) Wisman, Craig B. and John A. Waldhausen. "Aortic Valve Surgery." *Complications in Cardiothoracic Surgery.* Ed. John A. Wiseman and Mark B. Orringer. St. Louis: Mosby Year Book, date. 237–247.

2.) Cohn, Lawrence H. "Management of Complications Related to Mitral Valve Surgery." *Complications in Cardiothoracic Surgery.* Ed. John A. Wiseman and Mark B. Orringer. St. Louis: Mosby Year Book, date. 248–257.

Two types of prosthetic valves are currently available in cases where surgical treatment requires replacement of an aortic or mitral valve. These are bioprosthetics and mechanical prosthetics. Bioprosthetics are generally made from porcine or bovine material that may be attached to a metal or plastic frame. Although bioprosthetics are less thrombogenic than mechanical prostheses, they degenerate over time and must be replaced with another prosthetic device. Because of uncertain life expectancy and the associated need for replacement of bioprosthetics, mechanical prosthetics generally are preferred. Many mechanical prosthetic devices have been utilized since the 1960's with varying degrees of success. The development of these mechanical valves can be traced by reviewing the general classes or categories of mechanical prostheses.

Working independently, Hufnagel and Campbell designed the first prosthetic valve, which consisted of a Lucite tube and a mobile spherical poppet. Hufnagel was the first to use such a valve in the descending thoracic aorta of a human. Following the success of Hufnagel, the next advance in mechanical valves was the introduction of the caged-ball valves. Starr-Edwards first inserted such a valve in the mitral position, while Harken first positioned the valve in the aortic position. Caged-ball valves consist of generally three or four struts attached to a ring that is inserted in either the mitral or the aortic position. Contained within the valve struts is a silastic ball, which controls the flow of blood through the valve. To prevent thrombosis, which begins on the atrial surface of the device, a retractable Silastic shield was added to cover the suture line in the dog model, but this Silastic shield was abandoned when this valve was implanted in humans. A number of caged ball valves followed in the wake of the Starr-Edwards and Harken devices including the Serville-Arbonville, Harken-Daval, Cooley-Cromie, Debakey-Surgitool, and Smeloff-Cutter. These models were succeeded by improved designs and have been taken off the market. The Starr-Edwards caged-ball valve is still used today.

3.) Fann, James I., Carlos E. Moreno-Cabral, and D. Craig Miller. "Caged-Ball Valves: The Starr-Edwards and Smeloff-Sufter Prostheses." *Replacement Cardiac Valves.* Ed. Endre Bodnar and Robert Frater. New York: Pergamon Press, 1991. 149–186.

4.) Lefrak, Edward A. and Albert Starr, eds. *Cardiac Valve Prostheses.* New York: Appleton-Century-Crofts, date. 3–32.

Caged-ball valves belong in the class of lateral flow valves. Also developed at about the same time is a class of valves known as central flow valves, which are designed to imitate natural valves. Unable to endure the stress of repeated flexion, the materials available to create these valves did not prove sufficiently durable. Until more durable materials are developed, central flow valves have, by in large, been abandoned in favor of other types of lateral flow valves such as the tilting disk valves and the bileaflet valves.

5.) McGoon, D. C. "The Status of Prosthetic Cardiac Valves." *Biological Tissue in Heart Valve Replacement.* Ed. M. I. Ionescu, D. N. Ross, and G. H. Wooler. London: Butterworths, date. 3–17.

Compared to the caged-ball valves, tilting disk valves are designed to reduce the bulk of the earlier valves while improving hemodynamic characteristics. Tilting disk valves have a lower profile than caged-ball valves. Instead of a ball, these valves utilize a disk which is tilted such that blood flow is less obstructed in an open position. Most commonly used until 1982 was the Bjork-Shiley valve. This valve has a free-floating disk retained by a low-profile M-shaped strut on the inflow side and a U-shaped strut on the outflow side of the valve. The original version is capable of pivoting to an opening of 60 degrees, while later versions provided a convexoconcave shape and were available with an opening of either 60 or 70 degrees. However, a high incidence of failure due to breakage of the metal struts led to discontinued use of this valve. Today, the Omniscience and the Medtronic Hall valves are the most commonly used tilting disk valves in the United States.

6.) Bain, William H., and S. A. M. Nashef. "Tilting Disk Valves." *Replacement Cardiac Valves.* Ed. Endre Bodnar and Robert Frater. New York: Pergamon Press, 1991. 187–200.

Another type of low-profile heart valve prostheses is the bileaflet valve. First designed by Gott-Daggett, this valve replaces the ball or disk of the prior valves with two semicircular leaflets retained within the ring by two struts. While providing improved hemodynamics, the Goft-Daggeft lacked proper wash-out which made the device highly thrombogenic. The Gott-Gaggett valve is best known for being the impetus for the development of pyrolitic carbon, in particular, Pyrolite®. Pyrolite is a thromobresistant material that is particularly biocompatible. At the present time, Pyrolite, or other pyrolitic carbon material, is used to construct bileaflet valves, as well as the disks and one orifice design of the tilted disk valves. The most commonly implanted bileaflet valves are the Sultz-Carbomedics and St. Jude valves. For information concerning bileaflet valves, see 7.) Horstkotte, Dieter and Endre Bodnar. "Bileaflet Valves." *Replacement Cardiac Valves.* Ed. Endre Bodnar and Robert Frater. New York: Pergamon Press, 1991. 201–228.

Regardless of the type of prosthesis chosen, a similar procedure is followed for all mechanical valve implantations. First, the surgeon exposes the heart. Then, the aorta is clamped to cut-off the blood flow to the heart, and a heart-lung machine performs the heart's normal function, supplying blood to the rest of the body. After connecting the heart to the machine, the defective or diseased valve is exposed by making an incision in the aorta and the left atrium. Excision of the diseased tissue leaflets of the valve is then performed along with debridement of calcium using a Kelly clamp or pituitary rongeurs. After removing the natural valve leaflets, the surgeon places sutures through the surrounding heart valve tissue around the heart valve, drawing the sutures out of the chest of the patient. Everting sutures sometimes are used to prevent interference of the mechanical leaflets by retained native valve structures, chordal structures or by tips of papillary muscles. These sutures push the annulus of the prosthetic device away from the underlying tissue. Each suture is then drawn by needle through the cloth sewing ring that surrounds the replacement valve. To properly position the replacement valve, it is pressed down along the sutures, which act as guide wires. In addition to the use of everting sutures, proper positioning avoids interference with the device's moving parts. This is particularly true for valves such as the original St. Jude valve, which cannot be repositioned once sutured into place. When in the correct position, each suture is tied off in a knot with the end being trimmed.

There are a number of risks associated with open-heart surgery that are related to the duration of the procedure. Despite advances in blood conservation, the longer it takes to complete a surgical procedure the greater the chance the patient may need a transfusion, which carries with it the risk of transmitting diseases such as HIV or hepatitis, among others. Further, as noted in one text on blood conservation in cardiac surgery, " . . . a perfect operation in a patient that bleeds to death is a catastrophe." In addition to problems associated with blood loss and transfusion, a patient connected to a heart-lung machine during a valve replacement procedure may suffer memory loss after surgery. See 8.) Krieger, Karl H. and O. Wayne Isom, eds. *Blood Conservation in Cardiac Surgery.* City: Springer, 1997.

Other risks associated with mechanical valve procedures are paravalvular leakage and the need for subsequent replacements. Such leaks may be avoided by proper preparation of the heart valve tissue before placement of the prosthetic device, but if not successfully avoided paravalvular leaks result in excessive cardiac workload and the possibility of haemolysis with resulting anaemia.

A prosthetic valve suffering from excessive wear or mechanical failure must be replaced in a subsequent surgery. In subsequent surgeries the sutures holding the prosthetic device in place must be removed and a new device inserted and resutured to the surrounding tissue. After a number of replacements, the tissue surrounding the valve becomes perforated and scarred making attachment of each new valve progressively more difficult. See in this regard:

9.) U.S. Pat. No. 4,506,394, by Pierre Bedard, entitled "Cardiac Valve Prosthesis Holder," issued Mar. 26, 1985.

BRIEF SUMMARY OF THE INVENTION

The present invention is addressed to a heart valve prosthesis system and apparatus and to the method of its implantation. Characterized in permitting the carrying out of open heart surgical implantation procedures within a reduced interval of time, the valve prosthesis employs an implantable abutment structure in conjunction with a mechanical valve occluder function. This abutment structure incorporates a resilient metal substructure formed, for example, of a nickel-titanium alloy having an attachment portion which is released from a retracted orientation to elastically move into substantially permanent engagement with a native heart annulus. The metal substructure is fully covered with a porous layer such as a polymeric knit fabric having an interstitial structure selected to promote tissue ingrowth for the purpose of enhancing the valve-native annulus seal and provides a long term firm attachment.

The combined valve and abutment structure further is configured to provide a diminished widthwise dimension along a portion of its abutment structure which is implanted along the aortic valve-mitral valve region of mutual adjacency. Thus, an aortic heart valve prosthesis will not physically interfere with the adjacent mitral valve function and, conversely, a mitral valve prosthesis will not interfere with an adjacent aortic valve function.

The system utilizes a positioning instrument which includes a generally cylindrical aligning component which functions to retract the moveable attachment portion of the abutment structure as it is maneuvered to a location in adjacency with the native heart valve annulus. The prosthesis is slidably engaged within the cavity of the aligning component and is retained in a stabilized position with respect to the native heart annulus by a position stabilizer which extends within the cavity of the alignment component. Thus, the surgical procedure involves the slidable movement of the alignment component away from the heart valve prosthesis which in turn permits the movement of the attachment portion into engagement with the native heart annulus.

While the occluder valve function of the valve prosthesis seldom, if ever, would require replacement, by removably attaching that function to the abutment structure, subsequent valve replacement can be carried out. Preferably, the attachment is provided with sutures which can be severed in the course of valve replacement and a replacement valve can then be sutured to the abutment structure.

In one embodiment of the invention, the abutment structure includes a resilient metal substructure which is formed as a flat annulus having three radially outwardly extending tabs which engage the upper surface of the native heart annulus and the corresponding three retractable dog structures which move into engagement with the opposite side of the native heart annulus during the process of implantation. In another embodiment, the substructure is configured as an outwardly open generally torus-shaped structure formed with a mesh configuration wherein oppositely disposed sides constitutioning the attachment portion move into resilient engagement with the native heart annulus.

Other objects of the invention will, in part, be obvious and will, in part, appear here and after.

The invention, accordingly, comprises the method, system and apparatus possessing the construction, combination of elements, arrangement of parts and steps which are exemplified in the following detailed description.

For a fuller understanding of the nature and objects of the invention, reference should be had to the following detailed description taken in connection with the accompanying drawings.

DETAILED DESCRIPTION OF THE INVENTION

Figure 1:
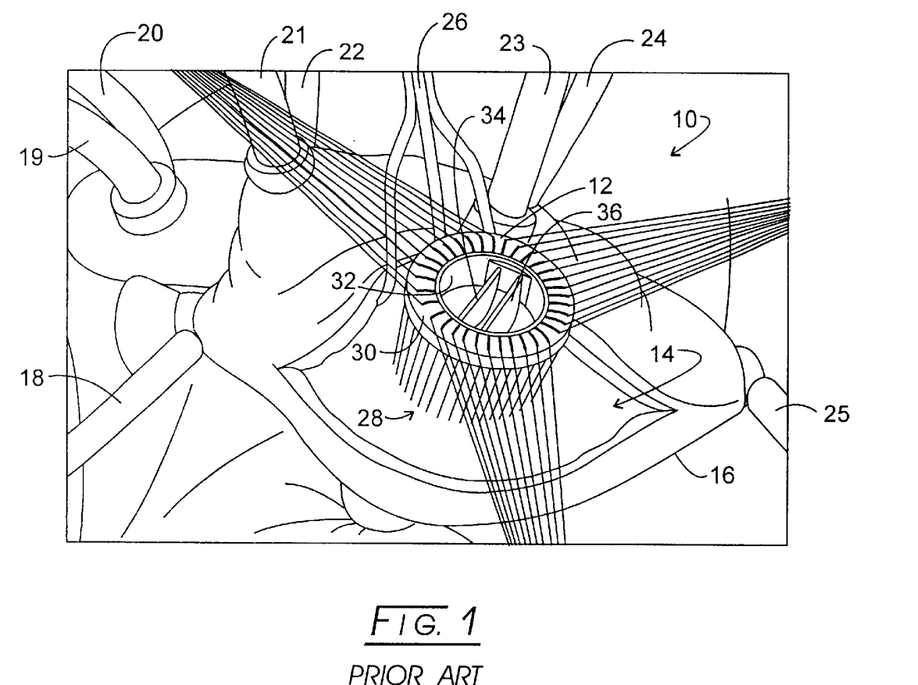
FIG. 1 is a pictorial representation of an event occurring during a prior art valve prosthesis implantation.

In the course of the procedure for implanting a prosthetic heart valve, the heart region is accessed and the heart is cannulated or pulmonary support is carried out by a cardiopulmonary by-pass machine. The blood supply thus being by-passed, the surgeon may access the interior of the heart. Typically these procedures are carried out to replace either or both the aortic valve and the mitral valve (left atrioventricular valve). Access to the valves for the procedure usually is made from the aortic and atrial side region of the heart. For example, in the carrying out of a mitral valve replacement procedure, the valve is exposed from the left atrium. Next, the native or natural tissue constituting the defective valve are excised. Following this initial preparation, the surgeon then places sutures entirely around the heart valve region and, particularly around the native annulus. Those, now elongate sutures then are drawn out of the chest and each then is inserted through a cloth sewing ring which surrounds the valve prosthesis. Thus, the mechanical valve is suspended outside of the chest at that point in time. This event in the procedure is pictorially represented in FIG. 1. Referring to that figure, the procedural event is represented generally at 10 wherein a mitral heart valve prosthesis 12 is suspended out of the chest above the exposed atrial region 14 of a heart 16. Hemodynamic components of the heart are seen coupled with conduit components of a cardiopulmonary by-pass machine as seen at 18–25. Exposure of the atrial region 14 is seen to be aided by a retractor 26. A vertical array of sutures 28 is seen extending from the native annulus of the diseased mitral valve to an attachment joining through the cloth sewing ring 30 of the prosthetic mitral valve 12. The valve 12 which is illustrated is one produced and marketed by Sulzer Carbomedics of Austin, Tex. and is formed with an interiorly disposed support ring 32 generally positioned within the sewing ring or cuff 30. Ring 32 is configured having pivot recesses to pivotally support an occluder formed of two leaflets 34 and 36. The support ring 32 and leaflets 34 and 36 are formed of a pyrolitic carbon identified in the industry as "Pyrolite", a very robust material which is biocompatible with the body. Not seen in the figure is a titanium reinforcement ring intermediate the support ring 32 and the sewing cuff 30 which protects the valve channel or orifice to minimize the risk of leaflet impingement or escape. Such valves as at 12 exhibit exceptional reliability and seldomly require replacement due to defective performance. The procedure following the procedural event 10 then is one wherein valve 12 is pressed down along the array of sutures 28 to an intra annular position within the natural annulus of the mitral valve. The array of sutures 28 perform somewhat as guidewires in this undertaking. Each of the sutures then is tied off with a knot functioning to hold down the valve in its proper position in the heart annulus and then the sutures are trimmed and closure procedures are undertaken. The patient's heart is stopped, for an uneventful operation, on the order of forty minutes plus or minus twenty minutes. Of that interval of time, the process of placing the sutures in the heart and tying knots therein along with the noted trimming represents the longest interval of the procedure. The function of the apparatus and system of the instant invention is to significantly reduce that time interval. This is achieved by combining the presently successful valve prosthesis structures with an abutment structure which performs in conjunction with a positioning instrument.

Figure 2:
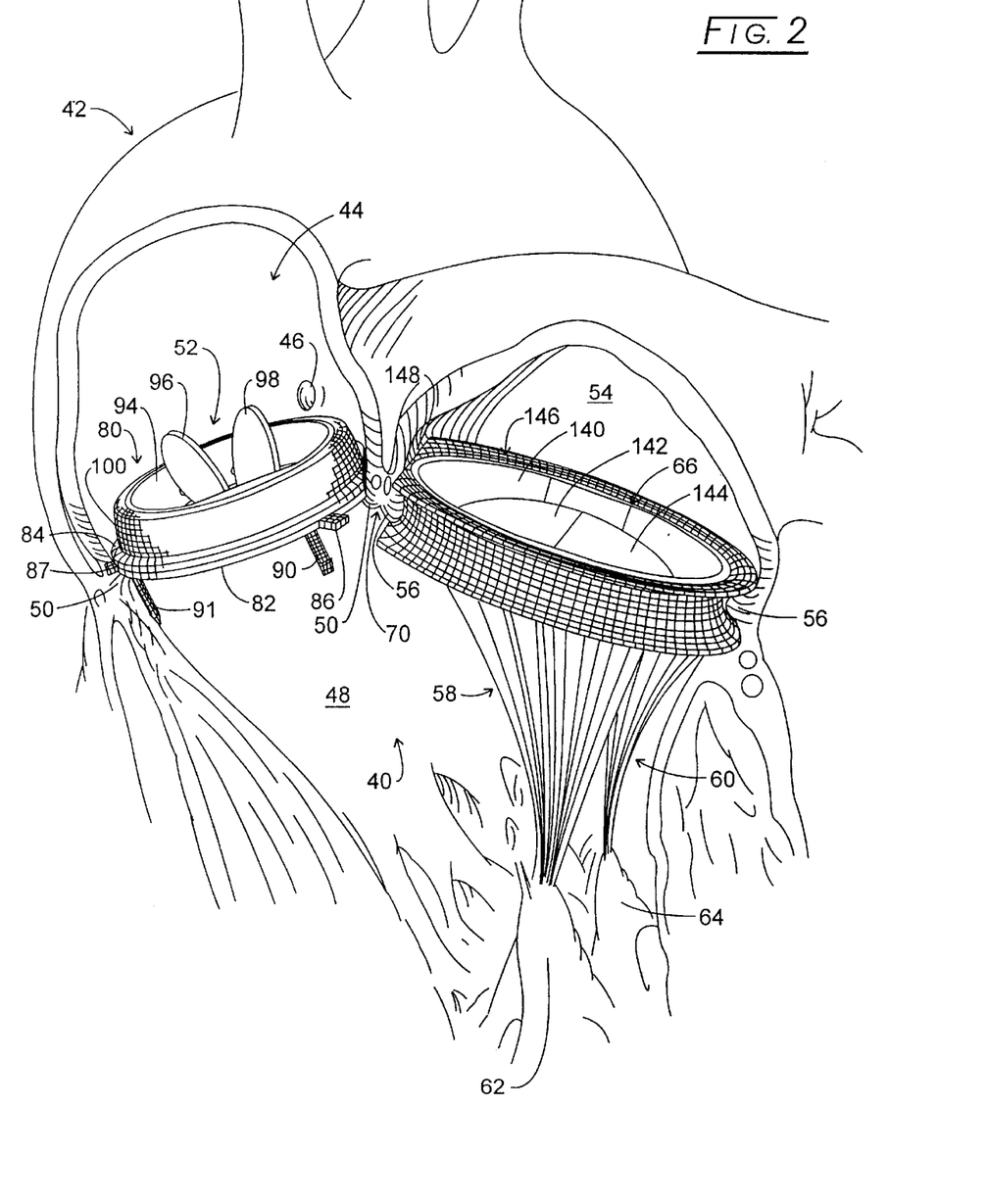
FIG. 2 is a pictorial representation of the implantation of an aortic and adjacent mitral valve prosthesis as implanted within a heart.

Referring to FIG. 2, an aortic and mitral valve prosthesis implantation is pictorially illustrated in general at 40. It is not uncommon that each of the aortic and mitral valves are replaced with a valve prosthesis. In the figure, the heart represented generally at 42 is illustrated sectionally to reveal the aorta 44, the left coronary artery 46 and the left ventricle 48. Intermediate the latter left ventricle 48 and aorta 44 is the location of the aortic valve, the scalloped heart valve annulus 50 remaining from the native valve. An aortic heart valve prosthesis represented generally at 52, is implanted supra-annually upon the heart annulus 50. In that regard, its lower or ventricular surface is abutably engaged with the arterial or supra-annular side of the annulus 50.

Left ventricle 48 also is in hemodynamic communication with the left atrium 54 through the mitral valve, the location of which now is represented by the mitral valve heart annulus 56. Additionally, chordae as at 58 and 60 are seen extending from respective papillary muscle 62 and 64. A mitral heart valve prosthesis configured according to the invention, is represented in general at 66 having been implanted in an intra-annular configuration. The figure reveals that the aortic valve function and the mitral valve function reside in relatively close adjacency. In this regard, the annuli 50 and 56 are juxtaposed at an aortic valve-mitral valve annulus region of mutual adjacency represented in general at 70. Accordingly, where a prosthesis is located at either the aortic valve position or the mitral valve position, it is important that the prosthesis not interfere with the adjacent valve function. The region of mutual adjacency 70 is in effect, a continuity between the adjacent two valve functions. It has been described as a thin, collagenous pars membranacea septi, an oval or round area below and partly confluent with the fibrous supports of the anterior (right coronary) and right posterior (non-coronary) aortic cuffs.

See: "Gray's Anatomy", 37$^{th}$ Addition, 1989 pp 708, 709, 717, Churchill Livingstone, New York, N.Y.

Now looking to the general structuring of aortic valve prosthesis 52, a currently marketed supra-annular annular aortic valve represented generally at 80, is removably coupled, for example, by suturing, to a cloth covered substantially permanently implantable abutment structure represented generally at 82. In this regard, the supra-annular annular or ventricular side of the abutment structure 82 is attached to the sewing cuff or ring 84 of the valve 80. The sub-annular or ventricular side of the structure 82 is positioned in abutment against the corresponding supra-annular side or atrial side of the heart annulus 50. Securement against blood flow back pressure is enhanced by an attachment portion which includes three radially extending attachment portions or tabs, two of which are seen at 86 and 87. Tissue located sub-annularly with respect to the annulus 50 is engaged, inter alia, by three resiliently outwardly biased dogs, two of which are seen at 90 and 91. Valve 80 is of a type which may be minimally altered or utilized without alteration, depending upon the dimensions involved, which is marketed by Sulzer Carbomedics (supra) under the trade designation "Top Hat". The valve has a support ring 94 with an occluder function comprised of two leaflets 96 and 98. Leaflets 96 and 98 are mounted with a recessed pivot design within the ring 94. As before, the orifice defined by the support ring 94 is exteriorly buttressed by a titanium stiffening ring (not shown) which is covered with cloth seen at 100. Support ring 94 and leaflets 96 and 98 are formed of the noted "Pyrolite" and the leaflets incorporate a tungsten impregnated substrate addition for purposes of enhancing their visibility by external imagining systems. Of course, the titanium ring additionally enhances that visualization. Note, at the region of mutual adjacency 70, the attachment portion of abutment structure 82 is reduced in its widthwise dimension to avoid interference with the mitral valve 66. Additionally, it may be observed that the dogs as at 90 and 91, as well as the outwardly extending tabs 86 and 87 are located without that region 70 of mutual adjacency. This assures that the aortic valve prosthesis will not interfere with the mitral valve function. It is preferred that the tabs as at 86 and associated dogs as at 90 be mutually offset but in somewhat close adjacency.

Figure 3:
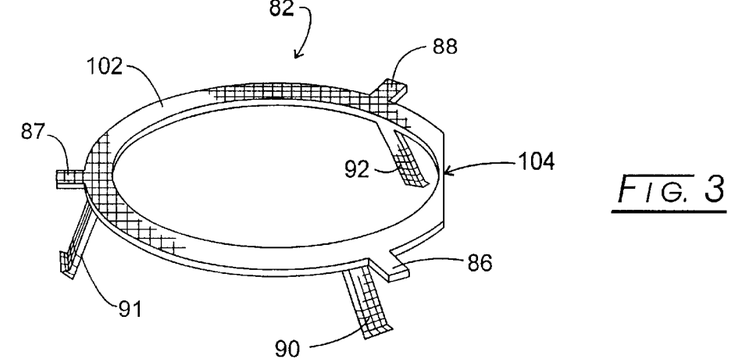
FIG. 3 is a prospective view of one embodiment of an abutment structure according to the invention.

Referring to FIG. 3, the abutment structure 82 is illustrated in enhanced detail. The figure reveals that the tabs 86–88 extend outwardly from a generally flat annulus 102 which has an outer periphery of diametric extent which is greater than the diameter of the native heart annulus associated with the aortic valve. Mounting provided by the annulus 102 and associated outwardly extending tabs 86–88 is super annular as revealed in FIG. 2. In this regard, the valve abutment structure is positioned above and upon the native annulus. With this arrangement, a more enhanced valve channel opening is made available. While the outer peripheral diameter of the abutment structure 82 will vary in dependence upon the aortic heart valve opening involved, the sizing of the tabs 86–88 is selected to assure the proper maintenance of the heart valve in its super-annular position. In this regard, the tab radial extent will be selected to maintain the valve position against back pressures occurring with valve closure. For example, back pressures may reach about 5 psi. Of critical importance, the tabs are positioned away from the above-noted region 70 of mutual valve adjacency. Additionally, the annulus 102 is configured having a widthwise dimension at region 104 for positioning at region 70 which is substantially reduced. In effect, the region 104 represents a configuration emulating the cord of a circle. Note, additionally, that the entire abutment structure 82 is formed or covered with a porous configuration or layer, the preferred embodiment being cloth. This cloth functions to promote the development of tissue ingrowth shortly following the implantation of the structure. The ingrowth material will fill the interstices of the cloth and develop an autogulous coating as well as a seal which is accepted by the immune system of the body. Such ingrowth will include thrombotic proteins. Thus, the attachment portion combination of tabs 86–88 and dogs 90–92 is sufficient to carry out the support of the supra-positioned heart valve. The covering cloth preferably is formed by knitting, a process by which needles are used to form one or more fibers into a series of interlocking loops. In this regard, one set of fiber is inter-looped as opposed to inter-laced. In addition to producing desired interstices for tissue ingrowth promotion, knit structures are more readily conformal to the substructure which they cover. The material utilized for the cloth may, for example, be a polyester or polytetrafluoroethylene. The positioning of the abutting structures 82 may be considered one where in its lower side may be deemed a "ventricular" side and the upper side may be deemed an "arterial" side. In the course of implantation, as disclosed in detail later herein, the ventricular side at the abutment structure is positioned in abutment with the arterial side of the heart annulus. The heart annulus region is engaged, not with sutures, but by the combination of the outwardly biased dogs 90–92 performing in conjunction with the tabs 86–88. As a consequence, those components must be well without the region 104 to avoid interference with the mitral valve function of the heart. In general, two of the tabs and adjacent dog combinations will be at the region of the coronaries, while the third combination of tab and dog will be positioned at a non-coronary location but outwardly from or without the region 104.

Figure 4:
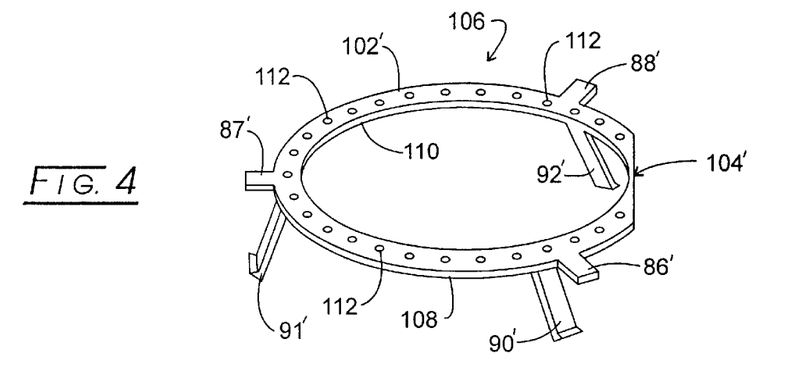
FIG. 4 is a prospective view of a substructure forming the abutment structure of FIG. 3.

Looking to FIG. 4, the metal substructure employed to form the abutment structure 82 is revealed generally at 106. The figure, as before, reveals that the tabs, now represented in primed fashion with the same numeration, extend from the outer periphery 108 of substructure 106. Note, additionally, that the dogs, now identified at 90'–92' extend from the inner circular periphery 110 of substructure 106. In general, a minimum of three such dogs are employed. The figure additionally reveals that the dogs 90'–92' are radially displaced from the radial locations of the tabs 86'–88' but are in relatively close adjacency with them. This displacement is provided to accommodate implantation procedure. To provide for that implantation procedure, the substructure 106 is formed of a resilient metal. In this regard, the substructure 106 may be formed of a highly elastic or shaped memory metal. The current preference for such metal is a nickel-titanium alloy which is commonly referred to as "Nitinol". This material can exhibit super-elastic properties permitting it to absorb substantial amounts of strain energy which is released as the applied strain is removed. As used herein, the term "resilient" is intended to mean either of the above highly elastic metal or shaped memory metal. Thus, the dogs 90'–92' can be restrained to a retracted position prior to emplacement at the heart annulus and then released for movement into an engaging or outwardly directed orientation. When employed in a shape memory biasing approach, the metals can be "taught" to move into an engaging and outwardly directed orientation with the application, for example, of heat as it is applied to the dogs subsequent to their being cooled while in a preparatory or retracted position.

While the prosthetic heart valve occluder structures which are employed with the abutment structure 82, exhibit excellent reliability, in view of the human application involved, it is also advantageous that they be capable of surgical removal and replacement in the event of any kind or form of mechanical failure. To accommodate for this aspect, an array of sewing apertures are formed within the flat annulus 102' certain of which are identified at 112. To permit replacement, the sewing ring 84 of valve 80 is sutured to the annulus 102 in connection with these apertures 112. Preferably, only a minor number of sutures are employed, for example, at three radial positions located at 120° spaced apart locations. The additional sewing apertures may the employed in connection with the reassembly of mechanical heart valves upon the annulus 102 for the rare occasions of a needed valve replacement. While the abutment structure 82 typically will remain in position with its thrombotic seal for such replacement occasion, its removal is facilitated inasmuch as only three dogs 90–92 need be severed.

Figure 5:
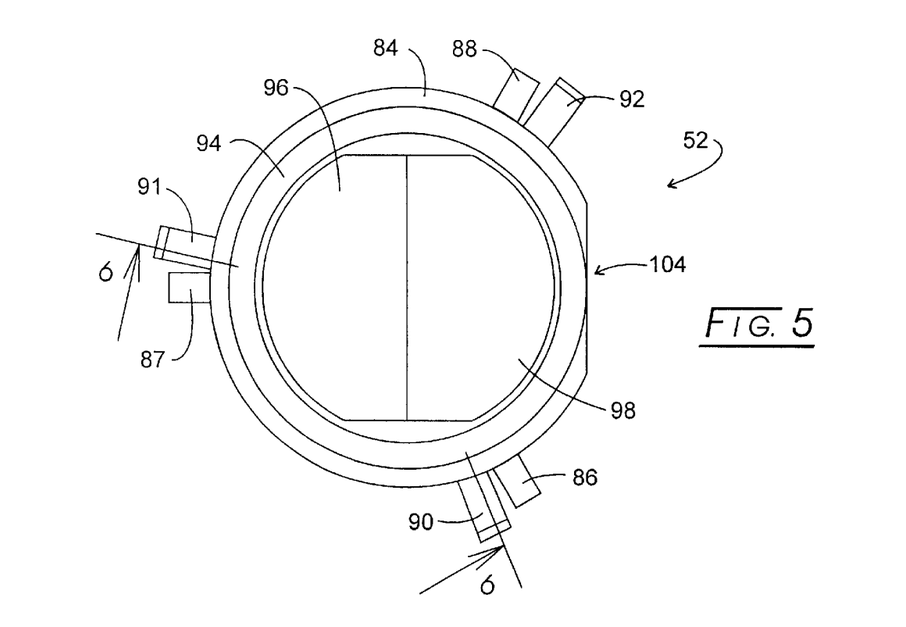
FIG. 5 is a top view of a heart valve prosthesis according to the invention.
Figure 6:
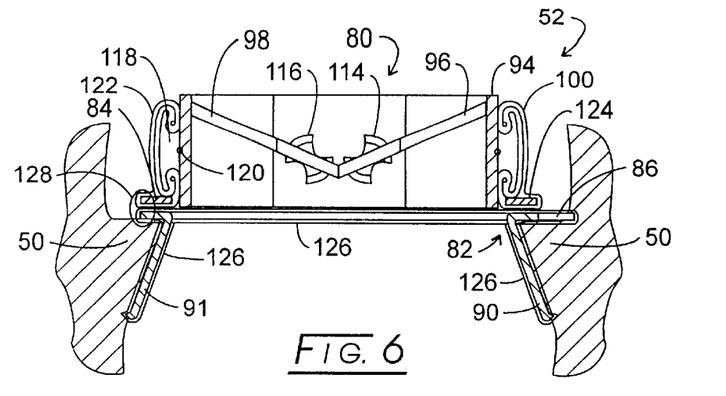
FIG. 6 is a sectional view taken through the plane 6—6 in FIG. 5.

FIG. 5 reveals a top view of the assemblage of abutment structure 82 and the supra-annular aortic valve 80. The figure reveals that the attachment structure comprising dogs 90–92 and the tabs 86–88 are well without the region 104. Looking additionally to FIG. 6, the features of the aortic valve and abutment structure are further delineated. Note that the bi-leaflets or leaflets 96 and 98 of the valve 80 are hinged within recessed in structures, two of which are revealed respectively at 114 and 116 and that the titanium stiffening or support ring 118 has a generally "T"-shape and is maintained in position by a titanium lock wire 120 which nests within a groove within the orifice 94. A knit cloth sewing ring or cuff is retained by the titanium stiffening ring 118 as shown at 122. Note that the sewing ring or cuff includes a needle penetrable rim 124 through which sutures are employed in conjunction with the sewing apertures 112 (FIG. 4) to retain the heart valve structure 80 upon the abutment structure 82. The cloth covering of that substructure is seen at 126. In the figure, dogs as at 90 and 91 are shown in engagement with the annular tissue at the ventricular side of the heart valve annulus 50. One suture as shown in FIG. 6 at 128 coupling the sewing ring 124 of the valve 80 with the annulus 102.

Returning to FIG. 2, the mitral valve prosthesis 66 is seen to be positioned intra- annularly. The valve component of it is formed with an orifice 140, the internal periphery of which typically supports two leaflets 142 and 144 which are hinged at a recessed hinged location and are shown in a closed orientation. Sutured to and supporting the orifice 140 is a cloth covered abutment structure 146 having an attachment portion which engages both the arterial and ventricular side of the heart annulus 56. Abutment structure 146 is seen to be configured as an outwardly open generally torus-shaped structure. Of importance, note that the abutment structure 146 has a restricted or reduced widthwise configuration at region 148 which is located along the region of mutual adjacency 70. As in the case of the aortic valve prosthesis, the mitral valve prosthesis thus configured, will not interfere with the performance of the aortic valve function.

Figure 7:
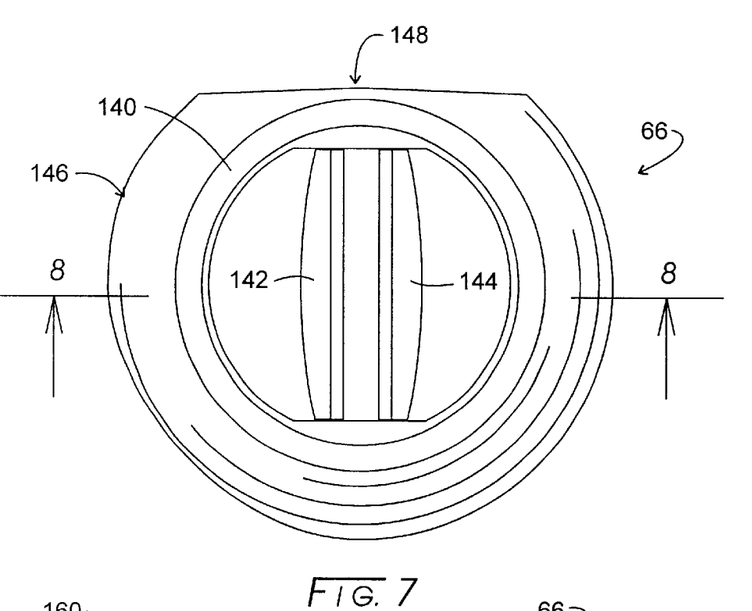
FIG. 7 is a top view of another heart valve prosthesis embodiment of the invention.
Figure 8:
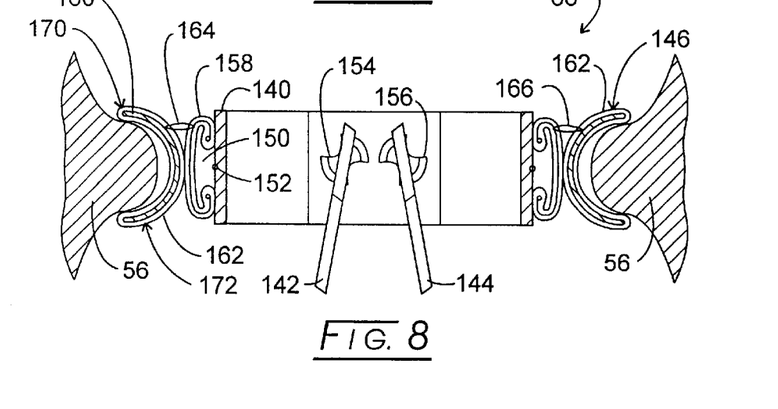
FIG. 8 is a sectional view taken through the plane 8—8 shown in FIG. 7.

Looking to FIG. 7, a top view of the mitral heart valve prosthesis is revealed. In the figure, the leaflets 142 and 144 are shown in an open orientation and region 148 of lessened widthwide extent is more clearly revealed. Only a small tissue capturing attachment is developed with the arrangement to avoid the noted potential interference with the aortic valve function. In FIG. 8, a cross section of the valve structure is revealed. Valve prosthesis 66 is formed of the same materials as employed in fabricating the above-described valve 52. Of additional similarity, the valve incorporates a generally T-shaped titanium stiffening ring 150 which is retained in position with a titanium lock wire 152 lock wire 152 is retained within an annular recess within stiffening ring 140. Leaflets 142 and 144 are shown hinged within recessed hinge cavities two of which are identified at 154 and 156. As before, the stiffening ring 150 is covered with a knit cloth 158. The abutment structure 146 is formed of the earlier described nickel-titanium alloy, being either on highly elastic or a shaped memory form of that alloy. The structure 146 includes a substructure form of the noted alloy which is configured with a mesh metal structure. That mesh metal structure, in turn, is covered with a knit cloth 162 and incorporates an attachment portion represented by an annulus-shaped upper side 170 and an annulus-shaped lower side 172. The cloth 162, containing interstices, functions, as before, as a tissue ingrowth promoting material which achieves a seal with the heart annulus 56. This thrombotic sealing activity commences essentially immediately upon the implantation of the abutment structure 146. To promote replaceability of the valve prosthesis 66, the sewing ring or cuff thereof represented by the combination of support ring 150 and cloth 158 is sutured to the cloth covering 162 of the abutment structure. Such sutures are represented in the figure at 164 and 166. Accordingly, the valve prosthesis 66 may be replaced with a simple expedience of severing sutures as at 162 and 164 and, in turn, suturing another valve 66 to the abutment structure cloth covering 162. Note that the sutures are located at the atrial side of a mitral valve or the aortic side for an aortic valve of the assembly. As before, the minimum number of such sutures is employed, for example, at three locations about the circumference of the valve prosthesis 66.

Figure 9:
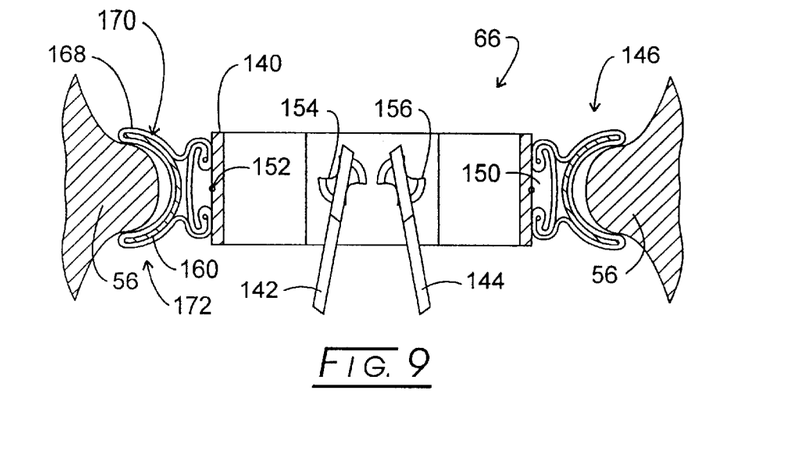
FIG. 9 is a sectional view taken through the plane 8—8 in FIG. 7 but showing an alternate attachment procedure for an abutment structure.

Looking momentarily to FIG. 9, another arrangement for carrying out this attachment is revealed. In the figure, components identical to those shown in FIG. 8, are identified with the same numeration. However, the cloth covering 168 is seen to be in common with both the substructure 160 and titanium support ring 50.

Figure 10:
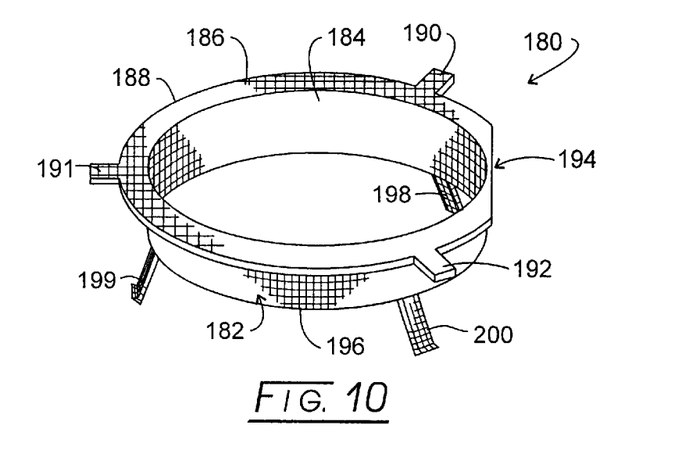
FIG. 10 is a prospective view of another abutment structure embodiment according to the invention.

The attachment portion of the abutment structure for a mitral valve prosthesis according to the invention also may be formed with a tab and dog structuring similar to that discussed in connection with FIGS. 3–6. Referring to FIG. 10, the abutment structure of this embodiment is revealed in general at 180. Formed of the same materials as the embodiment represented in FIGS. 4–6, the abutment structure 180 is configured having a cylindrical portion 182, the inner surface of which at 184 exhibits a diametric extent for receiving a mechanical heart valve. Integrally formed with the top edge of the cylindrical portion 182 is a flat circular annulus 186. Annulus 186 extends to an outer periphery 188 from which radially extends three tabs 190–192. Tabs 190–192 are generally spaced apart at 120° segments and reside without the region of the annulus 186 which has been removed such that it will be positioned at the earlier described region of adjacency 70 upon implantation. Region 194 is configured as the cord of a circle, only a small widthwise portion of the annulus extending outwardly from the outer surface of cylinder 182 for tissue engagement. As before, the annulus 186 has an upwardly disposed or atrial surface and an oppositely disposed ventricular surface which abuts against the atrial side of the annulus of a mitral heart valve. Tabs 190–192 are dimensioned radially to resist blood back pressure when the mitral valve prosthesis closed. Extending from the lower edge 196 and formed integrally with cylindrical portion 182 are three dogs 198–200 which are located in adjacency with respective tabs 190–192 but offset therefrom such that they may be retracted when located within a positioning instrument. As before, the entire substructure 180 is covered with a knit cloth or formed with an equivalent layer selected to promote tissue ingrowth to effect a seal of the abutment structure with the annulus of a heart at the mitral valve location. Not seen in FIG. 10 is an array of sewing apertures which may be formed in the annulus 186 and/or within the cylindrical portion 182 at a location adjacent the annulus 186. With such an arrangement, the mechanical heart valve sewing cuff may be attached to the abutment structure 180 utilizing sutures. Thus, as before, the mechanical valve component may be replaced should that be necessary.

Figure 11:
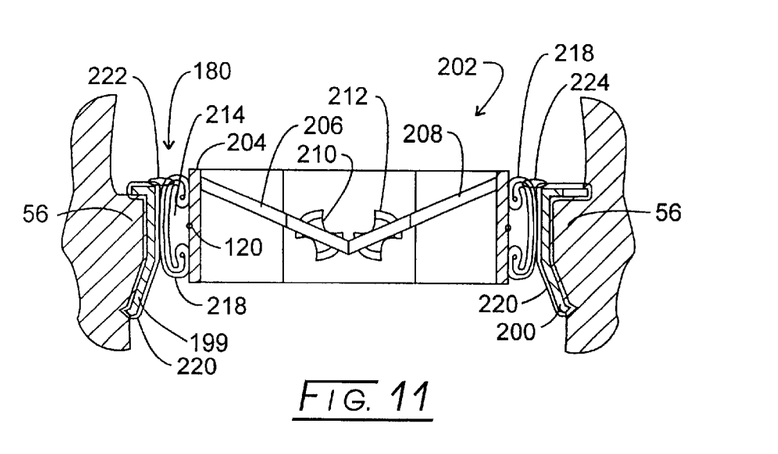
FIG. 11 is a sectional view of a heart prosthesis employing the abutment structure of FIG. 10.

Looking additionally to FIG. 11, a sectional view of the combined abutting structure and mechanical heart valve is revealed. In the figure, the mechanical heart valve prosthesis is represented generally at 202. As in the case of the valve structure shown in FIG. 8, the valve 202 is formed having a cylindrical orifice 204 and an inner valve channel within which is located an occluder function implemented by two pivotally mounted leaflets 206 and 208. Leaflets 206 and 208 are pivotally mounted within recessed pivot structures two of which are shown at 210 and 212. The ring orifice 204 is reinforced with a titanium support ring which is generally T-shaped shown at 214. Ring 214 is retained in position upon the support ring 204 by a titanium lock ring 120. Support ring 214 is covered with a knit cloth 218 which is retained in place by the ring itself. The knit cloth covering of the dog and tab components is seen in the figure at 220. Preferably, the valve structure 202 is attached to the abutment structure 180 by sutures, two of which are shown at 222 and 224.

Figures 12, 13:
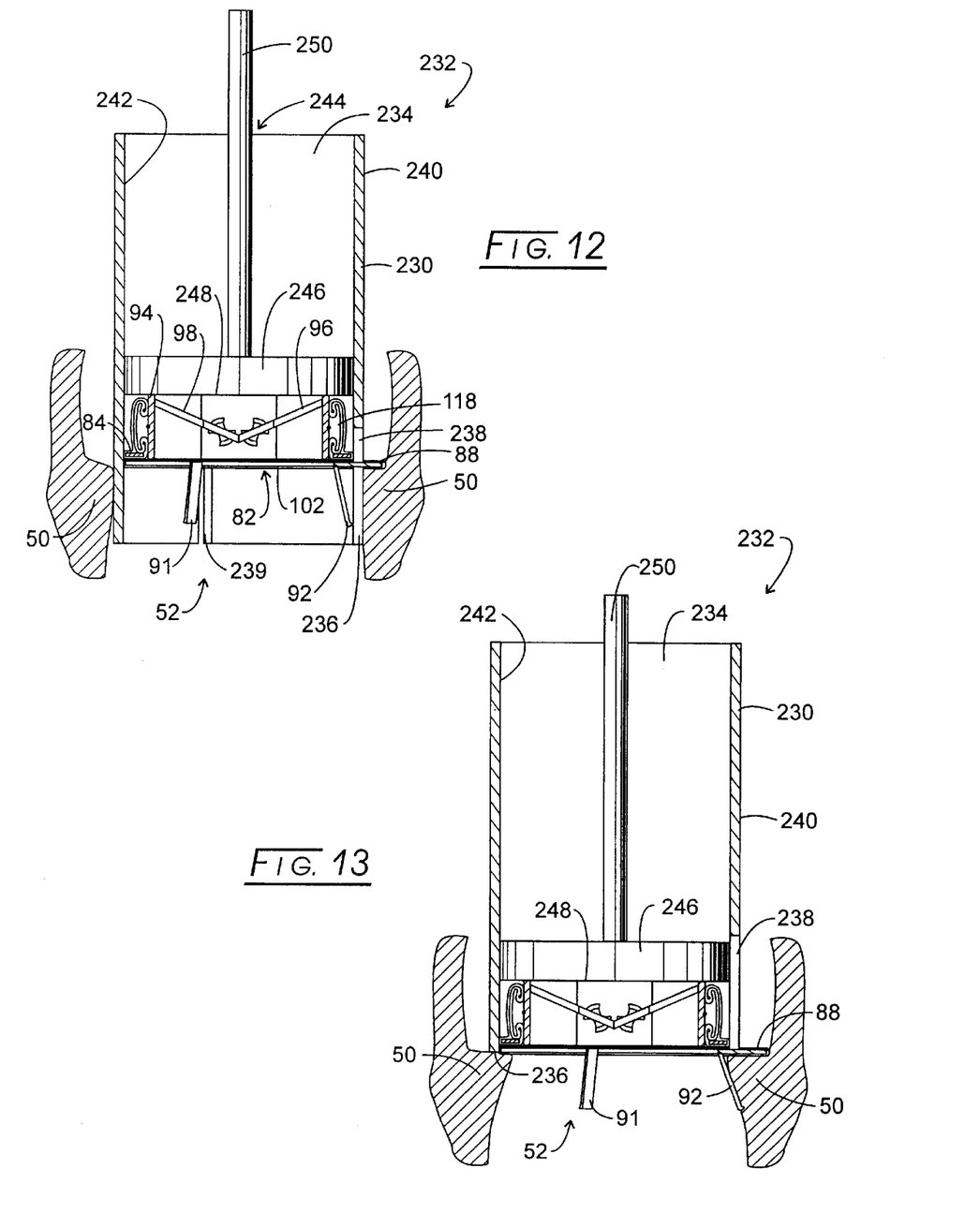
FIG. 12 is a sectional view showing an implantation step involving the heart valve prosthesis of FIG. 6.
FIG. 13 is a subsequent implantation maneuver following the step represented at FIG. 12.

The surgical implantation of the heart prosthesis of the invention is carried out utilizing a positioning instrument which retains the attachment portions such as the dogs of the embodiments of FIGS. 3 through 6 and 7–11 and the mesh sides of the embodiment of FIGS. 7 through 9 in retracted orientations as the prosthesis is positioned in adjacency with the annulus of the native heart valve. Referring to FIG. 12, the heart valve prosthesis embodiment of FIGS. 3 through 6 is shown slidably positioned within the aligning component 230 of a positioning instrument represented generally at 232. The aligning component 230 is formed as a right cylinder with a right cylindrical internal cavity 234 which extends to a lower generally cylindrical rim 236. Standing upwardly from rim 236 are three slots which are shown at 238 and 239. These slots are provided having a widthwise dimension corresponding with the widthwise dimension of tabs 86–88. In this regard, tab 88 is seen to extend through slot 238 tab 87 (not shown) extends through slot 239. With the arrangement, the tabs as at 88 extend through the slots and may be observed by the surgeon for appropriate positioning upon the supra-annular or atrial side of the native heart annulus 50. It may be recalled that dogs 90–92 reside in an offset adjacency with respect to respective tabs 86–88. Thus located, the dogs 90–92 are retained in a retracted orientation shown in FIG. 12 by virtue of their slidable engagement with the internal surface 242 of the aligning component 230.

Positioning instrument 232 also includes a position stabilizer represented generally at 244 which is slidably maneuverable within the internal cavity 234. In this regard, the stabilizer 244 includes a piston-like component 246, the lower surface 248 of which, freely abuttably engages the top of the heart prosthesis 52. The location of this lower surface 248 is stabilized by virtue of the connection of the piston-like component 246 with a hand manipulatable rod 250.

With the implantation procedure, following the mounting of the prosthesis 52 within the internal cavity 234 of aligning component 230, the aligning component is positioned to locate its rim 236 in adjacency with the ventricular side of the heart annulus 50 (below the annulus) and, for the instant embodiment, to position the tabs, representing a component of the attachment portion, into abutting adjacency with the upper supra-annular side or aortic side of the native heart annulus 50. The dogs 90–92 now are located for release into engagement with the native heart annulus at a region just beneath or on the lower or ventricular side of the native annulus. This orientation is shown in FIG. 12. The position stabilizer 244 now is used by the surgeon to stabilize the position of the heart valve prosthesis with respect to the heart annulus, i.e., in the orientation represented in FIG. 12. With the heart prosthesis 52 location stabilized, as represented in FIG. 13, the aligning component 230 is slidably moved upward and outwardly from the chest cavity. As this occurs, the dogs 90–92 are gradually released as the rim 236 ascends beside the stabilized heart prosthesis. Thus, dogs 90–92 are released for movement toward the adjacent heart tissue by virtue of their high resiliency or highly elastic nature. As part of the initial positioning, shown in FIG. 12, the region 104 (see FIG. 3) of restricted widthwise dimension of the prosthesis assembly is located in adjacency with the region of mutual adjacency of the native heart annulus as described in connection with FIG. 2. As is apparent, the entire procedure may be carried out in a relatively short interval of time, particularly a time much shorter than the time element associated with the procedure described in connection with FIG. 1.

Figure 14:
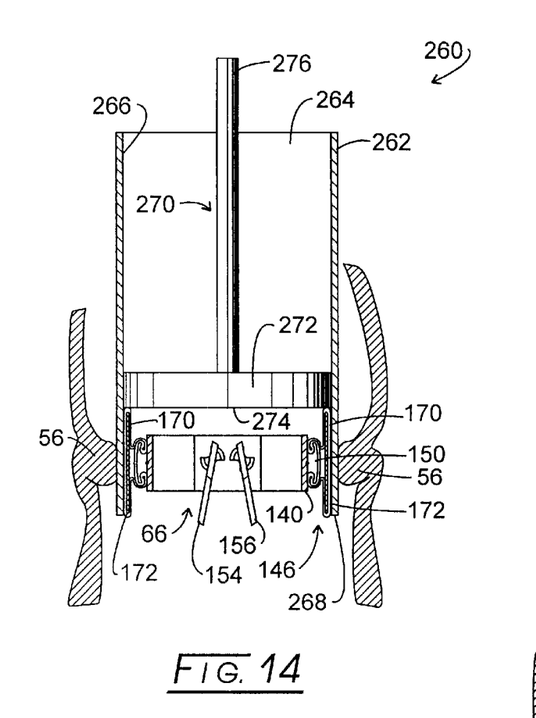
FIG. 14 is a sectional view representing an implantation step involving the heart valve prosthesis represented in FIG. 7.

Essentially the same implantation procedure is carried out in conjunction with the heart valve prosthesis described in connection with FIGS. 7–9. Looking to FIG. 14, a positioning instrument is represented generally at 260 as including a generally cylindrically shaped aligning component 262 having an internal cavity 264 with a cylindrically shaped internal surface 266 which, in turn, extends to a lower disposed rim 268. As in the earlier embodiment, instrument 260 additionally includes a position stabilizer represented generally at 270 which includes a piston-like cylindrical component 272 having a lower surface 274. The piston-like structure 272 is manipulatable by hand by virtue of a rod 276 attached thereto.

Slidably inserted within the cavity 264 is a mitral valve heart prosthesis as earlier described at 66. Accordingly, the components of the prosthesis 66 carry the same numeration as employed in conjunction with the description of FIGS. 7–9. Note in FIG. 14 that the upper annular side 170 of the substructure is restrained into a retracted orientation against the interior surface 266 as is the lower annular side which is seen to be positioned adjacent the lower rim 268. The lower surface 274 of position stabilizer 270 is in freely abutting engagement with the edge of annular side 170. Instrument 260 has positioned the prosthesis 166 at a location wherein the lower annular side of its substructure is located below or at the ventricular side of the native heart annulus 56. Correspondingly, the upper annular side 170 of the substructure is positioned above or upon the atrial side of the native heart annulus 56. Additionally, the earlier described region of diminished widthwise dimension as described at 148 in FIG. 7 will have been positioned adjacent the aortic valve-mitral valve annulus region of mutual adjacency.

Figure 15:
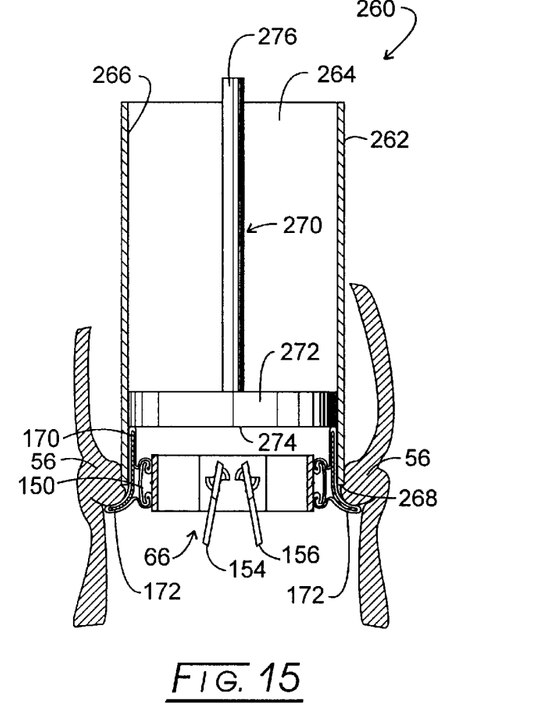
FIG. 15 is a sectional view showing a subsequenting event in the heart valve prosthesis implantation procedure of FIG. 14.
Figure 16:
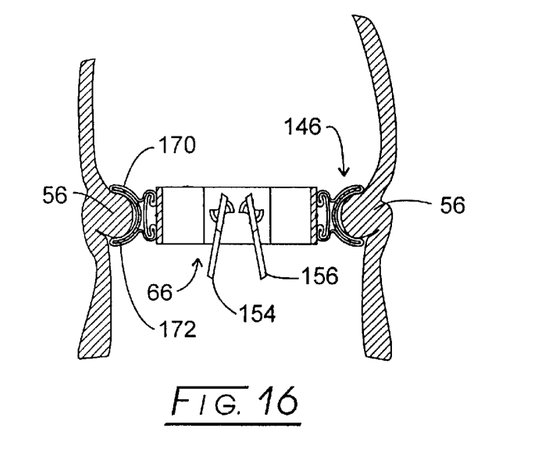
FIG. 16 is a sectional view showing a completed implantation of a heart valve prosthesis subsequent to the procedural event shown in FIG. 15.

FIG. 15 reveals the procedure wherein the physical location of the prosthesis 66 is maintained or stabilized by the position stabilizer 270 and the aligning component 262 is gradually elevated. At the position shown in FIG. 15, lower or ventricular annular side of the attachment portion of the substructure has been released from its retracted orientation to resiliently move into engagement with the ventricular side of the native heart annulus. Continued elevation of the alignment component 262 releases the upper annular side 170 from its retracted orientation such that the heart prosthesis 66 now is implanted now as seen if FIG. 16. As before, the system permits implantation of the heart prosthesis within a highly desirable much shorter interval of time.

Since certain changes may be made in the above described system, apparatus and method without departing from the scope of the invention herein involved, it is intended that all matter contained in the description thereof or shown in the accompanying drawings shall be interpreted as illustrative and not in a limiting sense.

What is claimed is:

1. A heart valve prosthesis for implantation at a heart valve annulus location having an aortic valve-mitral valve annulus region of mutual adjacency, comprising:
   A) a substantially permanently implantable abutment structure comprising a resilient metal substructure extending about a centrally disposed valve channel opening and having
      1) an attachment portion extending outwardly from said opening to define a first region having a widthwise first radial dimension selected for effecting resiliently biased engagement with said heart valve annulus at locations without said region of mutual adjacency;
      2) a second region having a widthwise second radial dimension less than said first radial dimension for engagement with said heart valve annulus within said region of mutual adjacency, said second widthwise dimension being effective to avoid substantial interference between the aortic and mitral valve functions; and
      3) a tissue ingrowth promoting porous layer located over substantially all surfaces of said substructure; and
   B) a heart valve comprising a support ring with an interior valve channel supporting a blood flow control occluder and having an outwardly disposed annular sewing cuff removably coupled with said abutment structure in a manner axially aligning said support ring with said centrally disposed valve channel opening.

2. The heart valve prosthesis of claim 1 in which said heart valve sewing cuff is attached to said abutment structure with sutures.

3. The heart valve prosthesis of claim 1 in which said porous layer is a tissue ingrowth promoting cloth.

4. The heart valve prosthesis of claim 3 in which said cloth is provided as an integral component of said annular sewing cuff to effect said removable coupling.

5. The heart valve prosthesis of claim 1 in which said attachment portion comprises an elastic metal engagement component biased for movement outwardly into tissue at the ventricular side of said heart valve annulus.

6. The heart valve prosthesis of claim 1 in which said attachment portion comprises an engagement component comprising a shape memory metal having a memory orientation for engaging tissue at the ventricular side of said heart valve annulus.

7. The heart valve prosthesis of claim 1 wherein:
   1) said metal substructure comprises an outwardly open, generally torus-shaped structure;
   2) said attachment portion comprises a first engagement portion for engagement with the aortic side of said heart valve annulus and a second engagement portion for engagement with the ventricular side of said heart valve annulus; and
   3) said heart valve support ring is coupled to said valve channel opening.

8. The heart valve prosthesis of claim 7 wherein at least one of said first and said second engagement portions comprises an elastic metal component biased for movement from a valve axial orientation outwardly toward said heart valve annulus.

9. The heart valve prosthesis of claim 7 wherein at least one of said first and said second engagement portions comprises a shape memory metal having a memory orientation biasing it for movement from a valve axial orientation outwardly toward said heart valve annulus.

10. The heart valve prosthesis of claim 1 wherein said second region is generally structured having an outer periphery configured as a chord of a circle defined by said first radial dimension.

11. The heart valve prosthesis of claim 1 wherein:
   A) said heart valve support ring comprises a diameter;
   B) said substructure comprises an annulus having an outer circular periphery corresponding to the diameter of the support ring;
   C) said attachment portion comprises three tissue engaging tabs extending outwardly from said circular periphery and three tissue engaging resiliently outwardly biased dogs;
   D) said sewing cuff comprises a flange extending outwardly from said heart valve support ring, said sewing cuff being removably coupled to said substructure annulus.

12. The heart valve prosthesis of claim 11 in which said substructure attachment portion tabs extend radially outwardly from said annulus outer periphery a distance effective to resist blood backflow pressure.

13. The heart valve prosthesis of claim 11 in which said substructure attachment portion tabs and dogs are located without said region of mutual adjacency.

14. The heart valve prosthesis of claim 11 wherein said sewing cuff is coupled to said substructure annulus with sutures.

15. The heart valve prosthesis of claim 11 in which:
   said substructure annulus includes an array of sewing apertures extending therethrough; and said heart valve sewing cuff is attached to said substructure annulus with sutures extending within said sewing apertures.

16. The heart valve prosthesis of claim 11 wherein said attachment portion dogs extend outwardly from said circular periphery at radial locations offset from the radial locations of said tabs.

17. The heart valve prosthesis of claim 16 in which said substructure attachment portion tabs and dogs are located without said region of mutual adjacency.

18. The heart valve prosthesis of claim 1 wherein:
   A) said substructure comprises a cylinder having a periphery, first and second ends, and a diameter, said cylinder further comprising a generally flat annulus extending radially outwardly from the periphery at said first end, said generally flat annulus having an aortic side and a ventricular side abuttable on the aortic side of said heart valve annulus;
   B) said attachment portion comprises three tissue engaging tabs extending outwardly from said periphery and three tissue engaging resiliently outwardly biased dogs extending from said second end of said cylinder; and
   C) said sewing cuff is coupled to said substructure adjacent the atrial side of said generally flat annulus.

19. The heart valve prosthesis of claim 18 in which said substructure attachment portion tabs extend radially outwardly from said annulus outer periphery a distance effective to resist blood backflow pressure.

20. The heart valve prosthesis of claim 18 in which said substructure attachment portion tabs and dogs are located without said region of mutual adjacency.

21. The heart valve prosthesis of claim 18 in which said mechanical heart valve sewing cuff is attached to said substructure with sutures.

22. The heart valve prosthesis of claim 18 in which:
   said substructure includes an array of sewing apertures extending there-through in the vicinity of said annulus; and
   said heart valve sewing cuff is attached to said substructure with sutures extending within said sewing apertures.

* * * * *